(12) United States Patent
Nyberg et al.

(10) Patent No.: US 6,773,898 B1
(45) Date of Patent: Aug. 10, 2004

(54) PROCESS CHALLENGE DEVICE

(75) Inventors: Russell Nyberg, Neola, IA (US);
Daniel J. Dwyer, Lincoln, NE (US);
Robert V. Dwyer, Jr., Omaha, NE (US)

(73) Assignee: Raven Biological Laboratories, Inc., Omaha, NE (US)

(*) Notice: Subject to any disclaimer, the term of this patent is extended or adjusted under 35 U.S.C. 154(b) by 11 days.

(21) Appl. No.: 10/238,436

(22) Filed: Sep. 9, 2002

(51) Int. Cl.[7] ................................. C12Q 1/22
(52) U.S. Cl. .................. 435/31; 435/287.4; 435/287.7; 435/288.7
(58) Field of Search ................. 422/58, 59; 435/31, 435/287.4, 287.7, 288.7

(56) References Cited

U.S. PATENT DOCUMENTS

| | | | |
|---|---|---|---|
| 4,248,973 A | * | 2/1981 | Kallies .................... 435/287.9 |
| 4,839,291 A | | 6/1989 | Welsh et al. ................. 435/296 |
| 5,866,356 A | | 2/1999 | Albert et al. .................. 435/31 |
| 5,922,592 A | * | 7/1999 | Tautvydas ................. 435/287.4 |
| 5,942,408 A | | 8/1999 | Christensen et al. .......... 435/31 |
| 6,268,209 B1 | * | 7/2001 | Pierson et al. ........... 435/287.9 |

* cited by examiner

*Primary Examiner*—David A. Redding
(74) *Attorney, Agent, or Firm*—Thomte, Mazour & Niebergall; Shane M. Niebergall

(57) ABSTRACT

A process challenge device and method of using the same is presented for testing the efficiency of various sterilization procedures on objects to be sterilized. The device is assembled from two tapered end portions having opposite open ends and an open pathway extending therethrough. A central chamber in the open pathway receives a Biological Indicator for testing the efficiency of the sterilization process. The device is ideal for testing a sterilization process on elongated objects such as tubing, at any point along their length. The coupling structures on the end portions provide the device with single-use security.

23 Claims, 2 Drawing Sheets

PROCESS CHALLENGE DEVICE

BACKGROUND OF THE INVENTION

1. Field of the Invention

The present invention relates to devices for testing the effectiveness of sterilization procedures and more particularly to process challenge devices using Biological Indicators to test the effectiveness of various sterilization procedures as the same are used to sterilize elongated objects.

2. Description of the Prior Art

Industries, including medical device manufacturing, health care, food packaging/preparation, and others, frequently require the sterilization of instruments and other objects. Sterilization procedures used in these industries may include steam, ethylene oxide gas, ionizing radiation, dry heat, hydrogen peroxide, chlorine dioxide, peracetic acid, ozone, plasma, and other related procedures.

The Association for Advancement of Medical Instrumentation ("AAMI") has published recommendations for testing steam and ethylene oxide sterilizers. Several forms of test packs containing Biological Indicators and other materials have been developed to challenge the parameters necessary for such sterilization. The AAMI defines Biological Indicators as a calibration of microorganisms of high resistance to the mode of sterilization being monitored, placed in or on a substrate, packaged to maintain the integrity of the inoculated substrate in a manner convenient to the ultimate user, which serve to demonstrate that sterilization conditions were met. For purposes of the present application, the foregoing general definition of Biological Indicators shall be adopted.

Current Biological Indicators are constructed to test the effectiveness of a sterilization procedure on elongated objects, such as tubing, at either the beginning or at the end of the tube only. This is simply due to the fact that most Biological Indicators simply cannot be placed into the center of a length of tubing due to size restrictions. Commonly used Biological Indicators are too large to fit into the narrow lumens of most sizes of tubing. A Biological Indicator is to be placed within the object being sterilized and can thus test the effectiveness of the sterilization process at that particular location. However, none of the Biological Indicators presently used are capable of testing the effectiveness of the sterilization process in the actual center of a length of tubing. Any Biological Indicator is only capable of testing the effectiveness of the sterilization process at the point where the Biological Indicator can be placed or located. Accordingly, when the testing device cannot locate the Biological Indicator at different points along the length of the catheter to be tested, one cannot be reasonably certain that the sterilization process being used will sterilize the full length of the tubing, including the center of the tubing length, which can be the most difficult area to sterilize.

What is needed is an in-line process challenge device for testing the effectiveness of a sterilization procedure on elongated structures, such as tubes, at select points along their length.

SUMMARY OF THE INVENTION

The process challenge device of the present invention is provided for use in testing the effectiveness of various sterilization procedures. In its preferred embodiment, the device is comprised of two substantially similar end portions, each having an open tapered end and an opposite end that is provided with a coupling flange. The coupling flanges of the two end portions are operatively connected to one another using a system of locking tabs and receptacles that are formed on the coupling surface of flanges. The tabs provide a connection that must be broken in order to separate the two end portions. Once separated, the two end portions cannot be rejoined, thus creating a single-use device.

When the two end portions are coupled to one another, the tapered openings in the two end portions are connected by an open pathway that extends through the process challenge device. An enlarged chamber is provided within the pathway, intermediate the tapered openings, to receive a Biological Indicator.

In use, the tapered end portions of the device are ideal for receiving the ends of tubing of various diameters. Accordingly, where it is desirable to test the efficiency of a sterilization process in the middle of a piece of tubing that is to be sterilized, a length of tubing can be severed into two pieces at the location to be tested. The two pieces of tubing are then connected to the tapered ends of the Biological Indicator. The sterilization process is then initiated, allowing the sterilant to proceed through the ends of tubing into the tubing's center area where the process challenge device is located. After the sterilization cycle is complete, the Biological Indicator can be aseptically removed from the device and incubated to determine whether sterilization was achieved at the location tested.

It is therefore a principal object of the present invention to provide an improved device for testing the efficiency of a sterilization process on elongated objects such as tubing.

A further object of the present invention is to provide an improved process challenge device for testing the efficiency of a sterilization procedure through the use of an "in-line" design.

Yet another object of the present invention is to provide a process challenge device that is capable of testing the efficiency of different sterilization procedures on various objects.

Still another object of the present invention is to provide a process challenge device for testing the efficiency of sterilization procedures using various forms of Biological Indicators.

Yet another object of the present invention is to provide a single use process challenge device for testing the efficiency of sterilization procedures on objects used in the medical device manufacturing, health care, or food preparation/packaging industries.

A further object of the present invention is to provide a process challenge device that protects the Biological Indicator from possible post-sterilization contamination from the time the process is complete to a later time when the Biological Indicator is cultured for growth/no growth testing.

Still another object of the present invention is to provide a process challenge device that is reasonably easy to manufacture and use.

These and other objects will be apparent to those skilled in the art.

DESCRIPTION OF THE PREFERRED EMBODIMENT

Figure 1:
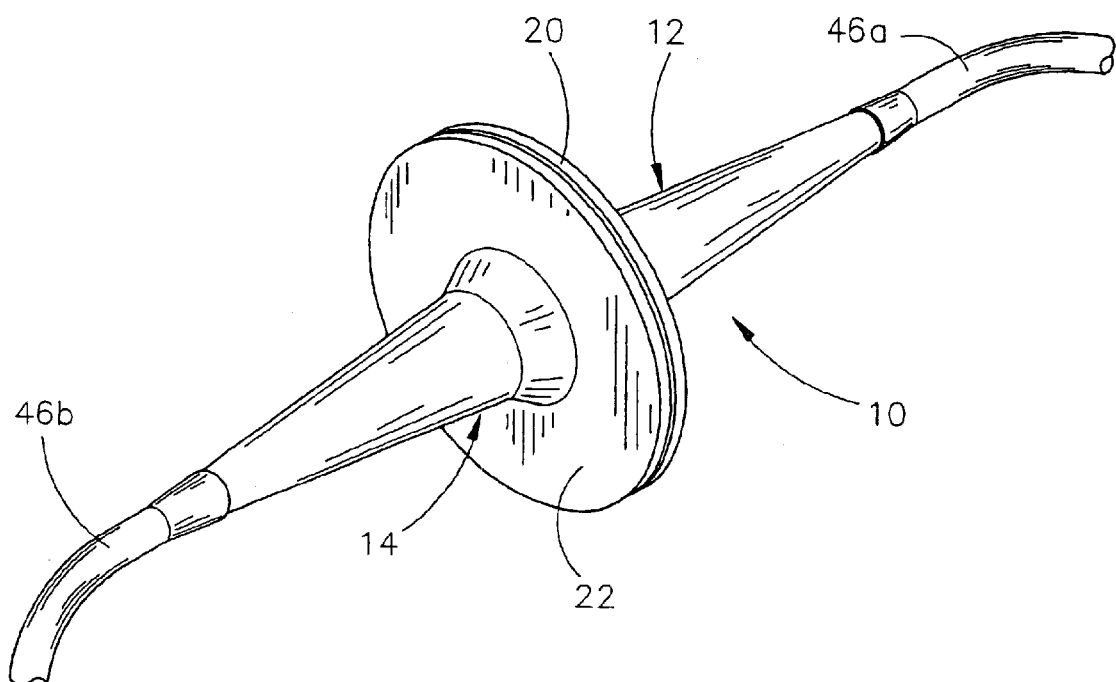
FIG. 1 is a perspective view of the process challenge device of the present invention as the device may be used in testing the effectiveness of a sterilization procedure on a piece of tubing.
Figure 3:
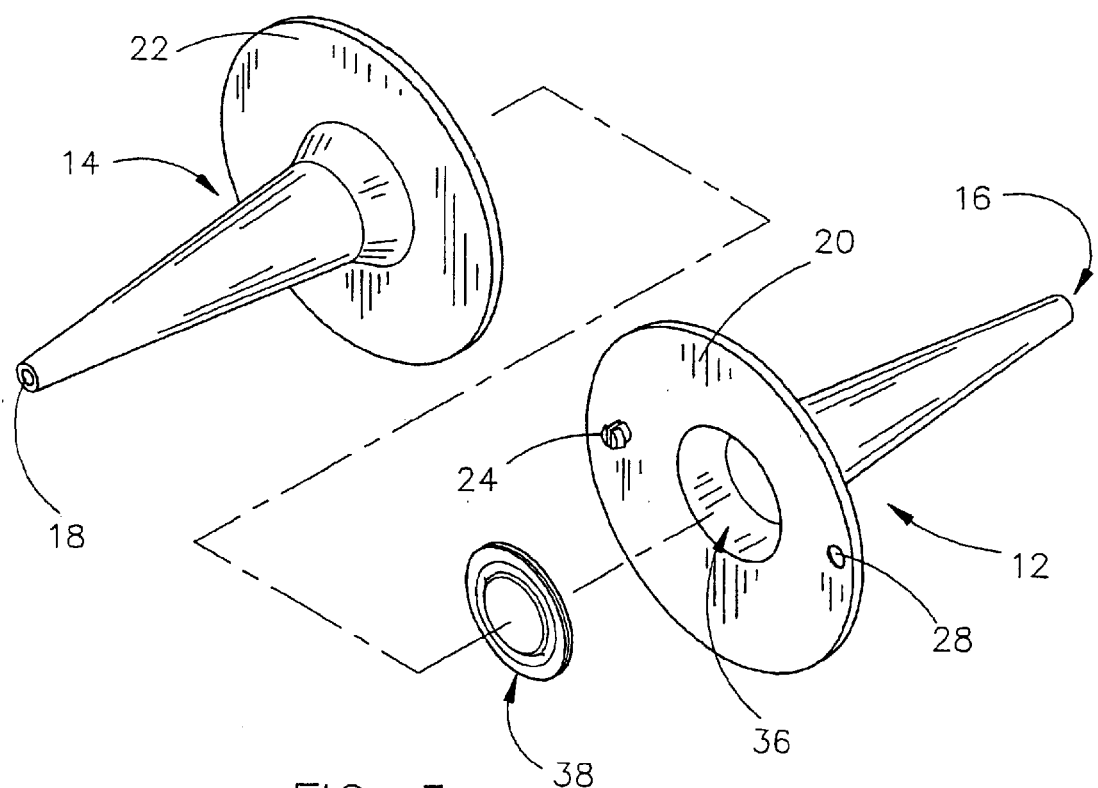
FIG. 3 is an exploded view of the process challenge device of FIG. 1 further depicting one type of Biological Indicator that can be used with the device.
Figure 2:
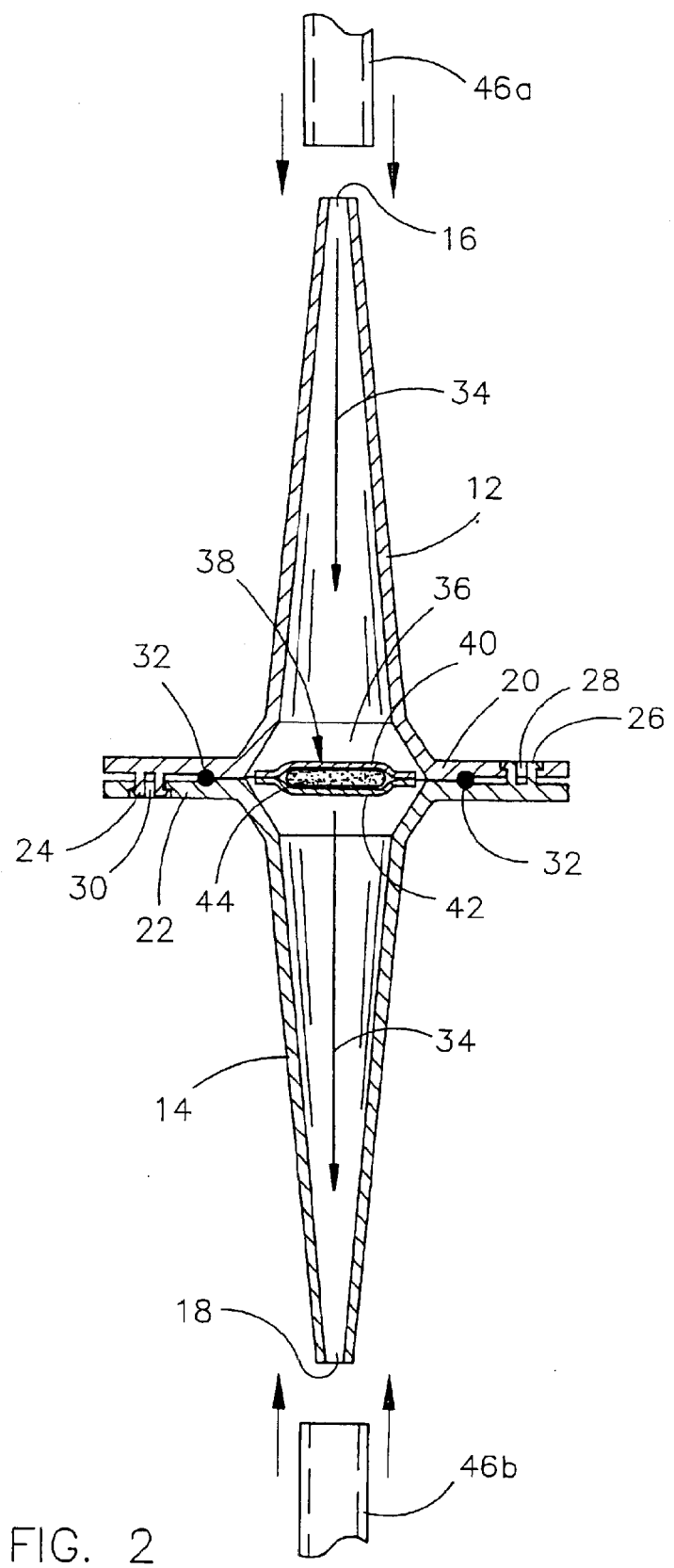
FIG. 2 is a cross-sectional view of the process challenge device of FIG. 1.

The process challenge device of this invention is referred to generally by the reference numeral 10 and is depicted in FIGS. 1, 2 and 3. For simplicity of description only, the process challenge device 10 of the present invention will be described as being used to test a sterilization process on a piece of rubber or plastic tubing, such as a catheter. It is contemplated that the process challenge device 10 described herein can be used to test a sterilization procedure on many other objects of similar and dissimilar structure.

The process challenge device 10 is preferably constructed of a material that is substantially liquid impermeable and substantially gas non-absorbant. In a preferred embodiment, the process challenge device 10 is comprised of two halves, a first end portion 12 and second end portion 14. The first and second end portions 12 and 14 are preferably constructed to be substantially similar for ease of manufacture and use of the device. However, it is contemplated that, to fit a particular testing situation, one end portion could be shaped or sized quite differently from the other end portion. Although the process challenge device 10 of the present invention will be described in terms of a general tubular shape, those skilled in the art will recognize that any shape permitting the flow of sterilant through a tortuous path that is dimensioned to provide intimate contact between the sterilant and a Biological Indicator comes within the intended scope of the present invention.

The first end and second end portions 12 and 14 are preferably shaped with a tapered cross-section, terminating in openings 16 and 18, respectively. The first and second end portions 12 and 14 are further provided with flanges 20 and 22, respectively. The flanges 20 and 22 provide the coupling surfaces upon which the first and second end portions 12 and 14 can be operatively connected. In a preferred embodiment, flange 20 is provided with a first locking tab 24 extending therefrom. The flange 22 is provided with a first receptacle 30. When the flanges 20 and 22 are positioned adjacent one another, the first locking tab 24 and first receptacle 30 align so that the first locking tab 24 can be secured within the first receptacle 30. It is contemplated that a second locking tab 26 will be provided on flange 22 and a second receptacle will be formed in flange 20. The second locking tab 26 and second receptacle 28 selectively engage one another in a manner similar to the first locking tab 24 and first receptacle 30. To provide for a single use process challenge device 10, it is preferred that the locking tabs be secured within their respective receptacles such that they cannot be separated without breaking the locking tabs from their respective flanges.

A gasket 32 is preferably disposed between flanges 20 and 22, as shown in FIG. 2, to at least substantially prevent the introduction of sterilant into the process challenge device 10 when it is in use. The gasket 32 can be made as a rubber or plastic O-ring or in other shapes and certain materials found to be desirable for the particular sterilization process being tested.

When first and second end portions 12 and 14 are coupled to one another, a pathway 34 is formed between openings 16 and 18. A portion of the pathway 34 is preferably enlarged to form a chamber 36 that can receive a Biological Indicator 38. The chamber 36 is preferably shaped and sized to accommodate the type of Biological Indicator 38 to be used.

While many different Biological Indicators could be used with the process challenge device 10, one of the preferred Biological Indicators is a disc comprising a first piece of glassine paper 40 and a second piece of glassine paper 42. A spore disc 44 is secured between the pieces of glassine paper. The glassine paper permits the penetration of the sterilization medium but prevents introduction of contamination from outside the Biological Indicator 38 and the transfer of spores from the spore disc 44.

With the assembly of the process challenge device 10, the sterilization procedure of the subject object can be tested. When it is desirable to test the middle portion of a section of tubing, the tubing is cut at the location to be tested. This creates a first section of tubing 46A and a second section of tubing 46B. The tapered portion of first end portion 12 is inserted into the cut end of tube section 46A. Likewise, the tapered portion of second end portion 14 is disposed within the cut end of tube section 46B. The opposite ends of tube sections 46A and 46B are then left open with these openings being the only place for sterilant entrance into the tube. The sterilization medium used by the sterilizer may include steam, ethylene oxide gas, hydrogen peroxide, chlorine dioxide, peracetic acid, ozone, plasma or other similar known sterilizing media.

Once the sterilization procedure is complete, the process challenge device 10 is disconnected from tubing sections 46A and 46B. The Biological Indicator 38 within the process challenge device 10 can now be evaluated. One preferable method of evaluating the Biological Indicator involves the transferal of the Biological Indicator 10 to a laminar flow hood after it is removed from the sterilizer. While in the laminar flow hood, the first end portion 12 and second end portion 14 can be separated from one another so that the Biological Indicator 38 can be easily removed from the chamber 36. The Biological Indicator 38 can then be processed and evaluated in accordance with the known methods of processing and evaluating the type of Biological Indicator being used to test the subject method of sterilization.

The process challenge device 10 provides an economical, disposable device for testing the efficiency of various sterilization procedures. The simplicity and versatility of the process challenge device 10 allows medical device manufacturing, health care, and food preparation/processing organizations to order one device for use and testing many different types of sterilization processes. Moreover, this single device can be used to test those areas of objects being sterilized that have been previously untestable, such as the middle portion of lengths of tubing.

In the drawings and in the specification, there have been set forth preferred embodiments of the invention; and although specified items are employed, these are used in a generic and descriptive sense only and not for purposes of limitation. Changes in the form and proportion of parts, as well as substitute of equivalents, are contemplated as circumstances may suggest or render expedient without departing from the spirit or scope of the invention as further defined in the following claims.

Thus, it can be seen that the invention accomplishes at least all of its stated objectives.

What is claimed is:

1. A device for testing the effectiveness of a sterilization procedure and a sterilant, the device comprising:

a housing having an open first end portion, an open second end portion, and an open pathway extending between said first and second end portions through which sterilant travels; and a Biological Indicator comprising a sample of biological organisms having known resistance characteristics;

said open pathway being adapted to receive the Biological Indicator so that the Biological Indicator is exposed to the sterilant during the sterilization procedure.

2. The device of claim 1 wherein the first end portion is shaped to generally taper toward the opening in said first end portion.

3. The device of claim 1 further comprising an indicator chamber formed in the pathway of said housing intermediate the openings of said first and second end portions.

4. An in-line process challenge device for testing the effectiveness of a sterilization procedure and a sterilant used during the sterilization procedure, the process challenge device comprising:

a first housing portion having a first opening and a first coupling surface;

a second housing portion having a second opening and a second coupling surface; said first and second coupling surfaces being adapted to be operatively connected to one another so that said first opening and said second opening are placed in open communication with one another and allow sterilant to pass through the device;

means for securing said first and second coupling surfaces to one another;

means for substantially preventing the sterilant from penetrating between the first housing portion and the second housing portion during the sterilization procedure; and a Biological Indicator positioned intermediate said first and second openings.

5. The device of claim 4 wherein the first housing portion is shaped to generally taper toward the first opening in said first housing portion.

6. The device of claim 5 wherein the second housing portion is shaped to generally taper toward the second opening in said second housing portion.

7. The device of claim 4 further comprising an indicator chamber formed in the pathway of said housing intermediate the first and second openings.

8. A method for testing the effectiveness of a sterilization procedure, comprising the steps of:

(a) providing a process challenge device, comprising:

(i) a housing having an open first end portion, an open second end portion, and an open pathway extending between said open first and second end portions through which sterilant travels; and (ii) a Biological Indicator disposed in said open pathway intermediate said open first and second end portions;

(b) operatively connecting the process challenge device to an object to be sterilized;

(c) subjecting the process challenge device and the object to a sterilization procedure; and (d) examining the Biological Indicator.

9. The method of claim 8 wherein said first end portion and said second end portion are separate structures; said first end portion being provided with a first coupling surface and said second end portion being provided with a second coupling surface; said first and second coupling surfaces being adapted to be operatively secured to one another.

10. The method of claim 9 further comprising a gasket disposed between the first coupling surface and the second coupling surface to substantially prevent the sterilant from penetrating between the first end portion and the second end portion during the sterilization procedure.

11. The method of claim 9 further comprising a first locking tab extending from the first coupling surface and a first receptacle formed in the second coupling surface; said first receptacle being adapted to operatively receive said first locking tab when the first end portion and the second end portion of said housing are operatively connected to one another.

12. The method of claim 11 further comprising a second locking tab extending from the second coupling surface and a second receptacle formed in the first coupling surface; said second receptacle being adapted to operatively receive said second locking tab when the first end portion and the second end portion of said housing are operatively connected to one another.

13. The method of claim 8 wherein the first end portion is shaped to generally taper toward the opening in said first end portion.

14. The method of claim 13 wherein the second end portion is shaped to generally taper toward the opening in said second end portion.

15. The method of claim 8 further comprising an indicator chamber formed in the pathway of said housing intermediate the open first and second end portions.

16. The method of claim 9 further comprising the step of separating the first end portion from the second end portion prior to examining the biological indictor.

17. The method of claim 16 wherein the first end portion and second end portion are separated so that an operative connection cannot be made between the first and second end portions after separation.

18. A device for testing the effectiveness of a sterilization procedure and a sterilant, the device comprising:

a housing having an open first end portion, an open second end portion, and an open pathway extending between said first and second end portions through which sterilant travels; and a Biological Indicator;

said open pathway being adapted to receive the Biological Indicator so that the Biological Indicator is exposed to the sterilant during the sterilization procedure;

said housing being comprised of material that is substantially liquid impermeable and substantially gas non-absorptive.

19. A device for testing the effectiveness of a sterilization procedure and a sterilant, the device comprising:

a housing having an open first end portion, an open second end portion, and an open pathway extending between said first and second end portions through which sterilant travels; and a Biological Indicator;

said open pathway being adapted to receive the Biological Indicator so that the Biological Indicator is exposed to the sterilant during the sterilization procedure;

said first end portion and said second end portion being separate structures; said first end portion being provided with a first coupling surface and said second end portion being provided with a second coupling surface; said first and second coupling surfaces being adapted to be operatively secured to one another.

20. The device of claim 19 further comprising a gasket disposed between the first coupling surface and the second coupling surface to substantially prevent the sterilant from escaping from between the first end portion and the second end portion during the sterilization procedure.

21. The device of claim 19 further comprising a first locking tab extending from the first coupling surface and a first receptacle formed in the second coupling surface; said first receptacle being adapted to operatively receive said first locking tab when the first end portion and the second end portion of said housing are operatively connected to one another.

22. The device of claim 21 further comprising a second locking tab extending from the second coupling surface and a second receptacle formed in the first coupling surface; said second receptacle being adapted to operatively receive said second locking tab when the first end portion and the second end portion of said housing are operatively connected to one another.

23. A device for testing the effectiveness of a sterilization procedure and a sterilant, the device comprising:

a housing having an open first end portion, an open second end portion, and an open pathway extending between said first and second end portions; and a Biological Indicator;

said open pathway being adapted to receive the Biological Indicator so that the Biological Indicator is exposed to the sterilant during the sterilization procedure;

said first end portion being shaped to generally taper toward the opening in said first end portion;

said second end portion being shaped to generally taper toward the opening in said second end portion.

* * * * *